United States Patent
Breton et al.

[11] Patent Number: 5,958,432
[45] Date of Patent: Sep. 28, 1999

[54] COSMETIC/PHARMACEUTICAL COMPOSITIONS COMPRISING β-ADRENERGIC AGONISTS/SUBSTANCE P ANTAGONISTS

[75] Inventors: Lionel Breton, Versailles; Olivier de Lacharriere, Paris; Jacques Leclaire, Massy, all of France

[73] Assignee: Societe L'Oreal S.A., Paris, France

[21] Appl. No.: 08/731,967

[22] Filed: Oct. 23, 1996

[30] Foreign Application Priority Data

Oct. 23, 1995 [FR] France .................................. 95-12447

[51] Int. Cl.⁶ ...................................................... A61K 7/48
[52] U.S. Cl. .............................. 424/401; 424/47; 424/49; 424/701; 424/450; 424/451; 424/464; 424/489; 514/844; 514/845; 514/846; 514/847; 514/861; 514/863; 514/885; 514/903; 514/912; 514/944
[58] Field of Search ...................... 424/401, 450, 424/701, 451, 464, 489, 47, 49; 514/844–847, 944, 861, 863, 885, 903, 912

[56] References Cited

U.S. PATENT DOCUMENTS

| | | | |
|---|---|---|---|
| 4,038,317 | 7/1977 | Nelson | 424/330 |
| 4,038,417 | 7/1977 | Nelson | 424/330 |

FOREIGN PATENT DOCUMENTS

| | | |
|---|---|---|
| 0120165 | 10/1984 | European Pat. Off. . |
| 0544391 | 6/1993 | European Pat. Off. . |
| 0612525 | 8/1994 | European Pat. Off. . |
| 0680749 | 11/1995 | European Pat. Off. . |

OTHER PUBLICATIONS

Chemical Abstracts, vol. 124, No. 4, Jan. 22, 1996, Columbus, Ohio, USA, Abstract No. 37409, XP002009203 and abstract of JP–A–07 258 067 (Kao Corp.), Oct. 9, 1995.

*Primary Examiner*—Jyothsna Venkat
*Attorney, Agent, or Firm*—Burns, Doane, Swecker & Mathis, L.L.P.

[57] ABSTRACT

Cosmetic/pharmaceutical compositions, well suited for the treatment of a variety of mammalian disorders of, for example, the skin, hair and/or mucous membranes, a manifestation of which is an excess in the synthesis and/or in the release of substance P, e.g., for the treatment of cutaneous disorders and sensitive skin, comprise an effective substance P antagonist amount of at least one β-adrenergic agonist, e.g., salbutamol, in a cosmetically/pharmaceutically acceptable medium therefor.

4 Claims, No Drawings

COSMETIC/PHARMACEUTICAL COMPOSITIONS COMPRISING β-ADRENERGIC AGONISTS/SUBSTANCE P ANTAGONISTS

BACKGROUND OF THE INVENTION

1. Technical Field of the Invention

The present invention relates to novel cosmetic/pharmaceutical compositions comprising at least one β-adrenergic agonist as a substance P antagonist, more particularly dermatological compositions, for the treatment of disorders associated with an excess in the synthesis and/or in the release of substance P.

This invention also relates to novel cosmetic/pharmaceutical compositions for topical application comprising at least one β-adrenergic agonist.

Too, this invention relates to a cosmetic/pharmaceutical treatment regime or regimen for decreasing the pain related to an excess in the synthesis and/or in the release of substance P, or for decreasing the irritant effect of a normally irritating compound, according to which a composition comprising at least one β-adrenergic agonist is topically applied onto the skin, onto the hair and/or onto the mucous membranes.

2. Description of the Prior Art

There exist in mammals polypeptides belonging to the family of tachykinins which induce rapid contractions with respect to smooth muscle fibers. Exemplary compounds of this family include neurokinin β, neurokinin α and substance P.

Substance P is a polypeptide (undecapeptide) chemical species developed and released by a nerve ending. Localization of substance P is specific to neurones, both in the central nervous system and in the organs at the periphery. Thus, a great many organs or tissues receive neurone afferences containing substance P, in particular the salivary glands, the stomach, the pancreas, the intestines (in the latter, the distribution of substance P is superimposed on Meissner's and Auerbach's intrinsic nerve plexus), the cardiovascular system, the thyroid gland, the skin, the iris and ciliary bodies, the bladder and, very obviously, the peripheral and central nervous systems.

Because of the ubiquitous distribution of substance P, a great many disorders are associated with an excess in the synthesis and/or in the release of substance P.

Substance P is involved, in particular, in the transmission of pain and in diseases of the central nervous system (for example anxiety, psychoses, neuropathies, neurodegenerative disorders of Alzheimer's senile dementia type, AIDS-related dementia, Parkinson's disease, Down's syndrome, Korsakoff's syndrome, multiple scleroses or schizophrenia), in respiratory diseases (such as, for example, bronchopneumonia) and inflammatory diseases (such as, for example, rheumatoid polyarthritis), in allergic syndromes (such as, for example, asthma, allergic rhinitis, allergic pharyngitis, urticaria or eczematous dermatitides), in gastrointestinal diseases (such as, for example, ulcers, colitis or Crohn's disease), in cutaneous disorders (such as, for example, psoriasis, pruriginous diseases, herpes, photodermatoses, atopic dermatitides, contact dermatitides, lichens, prurigo, pruritus, erythemas, in particular sunburn, or insect stings), in fibroses and other disorders of maturation of collagens (such as, for example, scleroderma), in cardiovascular disorders, in vasospastic disorders (such as, for example, migraines or Raynaud's disease), in immunological disorders, in disorders of the urinary tract (such as, for example, incontinence or cystitis), in rheumatic diseases, in certain dermatological diseases and in ophthalmological conditions (such as, for example, conjunctivitis, uveitides, ocular pruritus, ocular pains or irritations).

The administration of a substance P antagonist is one of the effective therapeutic alternatives in all of the conditions and afflictions indicated above.

By "substance P antagonist" is intended any compound capable of partially or indeed completely inhibiting the biological effect of substance P. In particular, for a substance to be recognized as a substance P antagonist, it must induce a coherent pharmacological response (including or not including its binding to the substance P receptor), in particular in one of the following tests:

(a) the antagonist substance must decrease the extravasation of the plasma through the vascular wall induced by capsaicin or by an antidromic nerve stimulation, or, alternatively;

(b) the antagonist substance must cause inhibition of the contraction of the smooth muscles induced by the administration of substance P.

To date, substance P antagonists are administered to treat the disorders indicated above.

SUMMARY OF THE INVENTION

It has now unexpectedly and surprisingly been determined that β-adrenergic agonists satisfy the criteria of substance P antagonists.

Thus, the present invention features the administration of at least one β-adrenergic agonist as a substance P antagonist in a cosmetic/pharmaceutical composition.

This invention also features cosmetic/pharmaceutical compositions comprising at least one β-adrenergic agonist for the treatment of disorders associated with an excess in the synthesis and/or in the release of substance P. Preferably, in the subject cosmetic/pharmaceutical compositions, the β-adrenergic agonist serves as a substance P antagonist.

DETAILED DESCRIPTION OF BEST MODE AND SPECIFIC/PREFERRED EMBODIMENTS OF THE INVENTION

More particularly according to the present invention, the subject compositions are advantageously formulated for topical application.

The present invention also features a cosmetic treatment regimen, according to which a cosmetic composition as described above is topically administered to a mammalian organism.

β-Adrenergic agonists are sympathomimetic molecules which reproduce the effects of stimulation of the sympathetic nerves.

Sympathomimetics act on the smooth muscle fibers. The prototype thereof is adrenalin. Receptors of different natures (α or β) and sympathomimetics which are more active with respect to certain receptors than with respect to others are distinguished. This is the case with β-adrenergic agonists which, as their name indicates, are specific for β-adrenergic receptors (themselves subdivided into 2 main subtypes, $B_1$ and $B_2$).

Compositions containing a β-adrenergic agonist for the treatment of excesses of grease on the human body (EP-A-120,165) or for the treatment of psoriasis (U.S. Pat. No. 4,038,417) or, alternatively, as an agent which can be used in baths for providing the skin with a feeling of freshness and the body with a feeling of warmth (JP-A-07,258,067) are known to this art. However, no prior art describes or suggests the involvement of substance P in the ailments or afflictions which the compositions described are intended to combat and still less any relationship between substance P and β-adrenergic agonists. The use of β-adrenergic agonists as substance P antagonists was hitherto unknown to this art.

Exemplary β-adrenergic agonists which are suitable for use according to the invention, include salbutamol, isoproterenol, CGP12177, nylidrin, salmeterol, fenoterol, terbutaline or pirbuterol.

Salbutamol is the preferred active agent according to the invention.

The amount of β-adrenergic agonist which is administered according to the invention is, of course, a function of the desired effect and of the nature of the agonist used.

For example, according to the invention, the agonist can be used in an amount by weight representing from $10^{-8}\%$ to 10% of the total weight of the composition and preferably in an amount representing from $10^{-5}\%$ to 4% of the total weight of the composition.

Examples of cutaneous disorders related to an excess in the synthesis and/or in the release of substance P are set forth hereinabove.

Thus, in a preferred embodiment of the invention, at least one β-adrenergic agonist is formulated into a cosmetic/pharmaceutical composition for the treatment of cutaneous disorders, such as, for example, psoriasis, pruriginous diseases, urticaria, atopic dermatitides, contact dermatitides, fibroses, disorders of maturation of collagen and generally pruriginous and/or erythemal dermatoses.

Moreover, in the field of cutaneous disorders, it is known that certain types of skin are more sensitive than others. Phenomena such as cutaneous irritations and/or sores and/or erythemas and/or dysaesthetic sensations and/or warming sensations and/or pruritus of the skin and/or of the mucous membranes are often associated with this increased sensitivity.

However, the symptoms of sensitive skins were, until now, poorly characterized and the problem of these skins was, for this reason, poorly defined. Indeed, the process implicated in the sensitivity of the skin was not exactly known. Some thought that a sensitive skin was a skin which reacted to cosmetic products, others that it was a matter of a skin which reacted to a number of external factors, not necessarily related to cosmetic products. Sensitive skins were also classified as allergic skins.

Tests have been developed in order to define sensitive skins, for example tests with lactic acid and with DMSO, which are known to be irritant substances: see, for example, the article by K. Lammintausta et al, *Dermatoses*, 36, pages 45–49 (1988) and the article by T. Agner and J. Serup, *Clinical and Experimental Dermatology*, 14, pages 214–217 (1989).

Due to ignorance of the characteristics of sensitive skins, it was, until now, very difficult, indeed impossible, to treat them. Indeed, they were treated indirectly, for example by limiting the employment in cosmetic or dermatological compositions of products with an irritant nature, such as surfactants, preservatives or fragrances, as well as the employment of certain cosmetic or dermatological active principles.

After many clinical tests, the symptoms related to sensitive skins have now been determined. These symptoms are in particular subjective signs which are essentially dysaesthetic sensations. By "dysaesthetic sensations" are intended more or less painful sensations experienced in a cutaneous region, such as smarting, pins and needles, itching or pruritus, burning sensations, warming sensations, discomfort, stabbing pains, and the like.

The assignee hereof has been able to demonstrate, in addition, that a sensitive skin was not an allergic skin. In fact, an allergic skin is a skin which reacts to an external agent, an allergen, which triggers an allergic reaction. This relates to an immunological cascade which only occurs when an allergen is present and which only affects sensitized subjects. In contrast, the essential characteristic of sensitive skin is, according to the assignee hereof, a mechanism of response to external factors which can concern any individual, even if individuals said to have sensitive skins react thereto faster than other individuals. This mechanism is not immunological: it is non-specific.

Thus, it has been found that sensitive skins could be divided into two major clinical forms: irritable and/or reactive skins and intolerant skins.

An irritable and/or reactive skin is a skin which reacts by a pruritus, namely, by itching or by smarting, to different factors, such as the environment, the emotions, food, the wind, friction, shaving, soap, surfactants, hard water with a high calcium concentration, temperature variations or wool. In general, these signs are associated with a dry skin, with or without sores, or with a skin which exhibits an erythema.

An intolerant skin is a skin which reacts with sensations of warming, stabbing pains, pins and needles and/or redness to different factors, such as the environment, the emotions, food and certain cosmetic products. In general, these signs are associated with a hyperseborrhoeic or acneic skin, with or without sores, and with an erythema.

"Sensitive" scalps have a less ambiguous clinical symptomatology: the sensations of pruritus and/or of smarting and/or of warming are essentially triggered by local factors such as friction, soap, surfactants, hard water with a high calcium concentration, shampoos or lotions. These sensations are also sometimes triggered by factors such as the environment, the emotions and/or food. An erythema and a hyperseborrhoea of the scalp and a dandruff state are frequently associated with the above signs.

Moreover, in certain anatomical regions, such as the major folds (inguinal, genital, axillary, popliteal, anal, submammary or bend of the elbow regions) and the feet, sensitive skin is reflected by pruriginous sensations and/or dysaesthetic sensations (warming or smarting) related in particular to sweat, to friction, to wool, to surfactants, to certain cosmetic preparations, to hard water with a high calcium concentration and/or to temperature variations.

In order to determine if a skin is sensitive or not, the assignee hereof has also developed a test. Indeed, after having carried out a great number of tests with the aim of defining a sensitive skin, it has been found that there existed a connection between people with sensitive skins and those who reacted to a topical application of capsaicin.

The test with capsaicin entails topically applying, to approximately 4 cm² of skin, 0.05 ml of a cream comprising 0.075% of capsaicin and in noting the appearance of subjective signs caused by this application, such as smarting, burning sensations and itching. In subjects with sensitive skins, these signs appear between 3 and 20 minutes after application and are followed by the appearance of an erythema which begins at the periphery of the application region.

To date, capsaicin has been used as a medicament, in particular for treating the pain from shingles. Capsaicin causes release of neuropeptides and in particular of tachykinins which emanate from nerve endings in the epidermis and in the dermis. It has been found that the physiopathologic scheme common to all sensitive skin states was related to a great ability to release tachykinins and more particularly substance P in the skin. The dysaesthetic manifestations which are caused by their release are known as "neurogenic".

A connection between substance P and sensitive skin had not hitherto been established. The clinical signs of sensitive skin are essentially subjective: smarting, pins and needles, pruritus, stabbing pains or warming and they are sometimes associated with erythemas. These signs are due to non-specific external factors. The symptoms appear essentially localized on the face, on the neck and on the scalp, but can also appear anywhere on the body.

Thus, it has now been determined that one of the essential characteristics of sensitive skins is related to the release of substance P and thus that the use of substance P antagonists can make it possible to obtain a preventive and/or curative effect with respect to sensitive skins.

Thus, the substance P antagonists have been proposed for the treatment of sensitive skins. Indeed, it has surprisingly been found that the incorporation of a substance P antagonist into a composition for topical application prevents irritation and/or dysaesthetic sensations and/or pruritus of the skin.

The present invention thus more particularly features the formulation of at least one β-adrenergic agonist into a cosmetic/pharmaceutical composition, these compositions being intended for the treatment of sensitive skins.

The present invention more particularly features the formulation of at least one β-adrenergic agonist into cosmetic/pharmaceutical compositions, such compositions being used to prevent and/or to combat cutaneous irritations and/or sores and/or erythemas and/or warming and/or dysaesthetic sensations and/or pruritus of the skin and/or the mucous membranes.

The β-adrenergic agonist can be formulated into a composition which must be ingested, injected or preferably topically applied onto the skin (over any cutaneous region of the body), the hair, the nails or the mucous membranes (buccal, jugal, gingival, genital, anal or conjunctive). Depending on the mode of administration, this composition can be provided in all of the pharmaceutical dosage forms normally employed.

For injection, the composition can be provided in the form of an aqueous lotion or of an oily suspension or in the form of a serum. For the eyes, it can be provided in the form of drops and, for ingestion, it can be provided in the form of capsules, of granules, of syrups or of tablets.

The β-adrenergic agonist is more particularly formulated into a composition for topical application.

Thus, this invention also features cosmetic or pharmaceutical compositions for topical application comprising at least one β-adrenergic agonist.

For topical application onto the skin, the composition can have the form, in particular, of an aqueous solution or oily suspension, or of a dispersion of the lotion or serum type, of emulsions having a liquid or semi-liquid consistency of the milk type, obtained by dispersion of a fatty phase in an aqueous phase (O/W) or vice versa (W/O), or of suspensions or emulsions with a soft consistency of the cream or aqueous or anhydrous gel type, or alternatively of microcapsules or microparticles, or of vesicular dispersions of ionic and/or nonionic type. These compositions are formulated via the usual techniques.

They can also be applied to the hair in the form of aqueous, alcoholic or aqueous/alcoholic solutions, or in the form of creams, gels, emulsions or foams, or alternatively in the form of aerosol compositions also comprising a pressurized propellant agent.

The amounts of the different constituents of the compositions according to the invention are those conventionally used in the fields under consideration.

These compositions constitute, in particular, cleansing, protection, treatment or care creams for the face, for the hands, for the feet, for the large anatomical folds, or for the body (for example day creams, night creams, makeup removal creams, foundation creams or anti-sun or sunscreen creams), liquid foundations, makeup removal milks, protective or care body milks, anti-sun or sunscreen milks, lotions, gels or foams for caring for the skin, such as cleansing lotions, anti-sun or sunscreen lotions or artificial tanning lotions, bath compositions, deodorizing compositions comprising a bactericidal agent, aftershave gels or lotions, depilatory creams, compositions for combating insect stings, pain-control compositions or compositions for treating certain diseases of the skin, such as eczema, rosacea, psoriasis, lichens or severe pruritus.

The subject compositions can also comprise solid preparations, e.g., cleansing bars or soaps.

The subject compositions can also be packaged in the form of an aerosol composition also comprising a pressurized propellant agent.

The β-adrenergic agonist according to the invention can also be incorporated into various compositions for hair care and in particular shampoos, hair-setting lotions, treating lotions, styling creams or gels, dye compositions (in particular oxidation dyes), optionally in the form of color-enhancing shampoos, hair-restructuring lotions, permanent-wave compositions (in particular compositions for the first step of a permanent wave), lotions or gels for combating hair loss, shampoos for combating parasites, and the like.

The compositions can also be for oral use, for example a toothpaste. In this case, the compositions can contain adjuvants and additives usual for compositions for buccal use and in particular surface-active agents, thickening agents, moisturizing agents, polishing agents such as silica, various active ingredients such as fluorides, in particular sodium fluoride, and optionally sweetening agents, such as sodium saccharinate.

When the composition is an emulsion, the proportion of the fatty phase can range from 5% to 80% by weight, and preferably from 5% to 50% by weight, with respect to the total weight of the composition. The oils, the waxes, the emulsifiers and the coemulsifiers used in the compositions in the emulsion form are selected from among those conventionally used in the cosmetics field. The emulsifier and the coemulsifier are present, in the composition, in a proportion advantageously ranging from 0.3% to 30% by weight, and preferably from 0.5 to 20% by weight, with respect to the total weight of the composition. The emulsion can, in addition, contain lipid vesicles.

When the composition is an oily gel or solution, the fatty phase can constitute more than 90% of the total weight of the composition.

In known manner, the cosmetic composition can also contain adjuvants which are conventional in the cosmetics field, such as hydrophilic or lipophilic gelling agents, hydrophilic or lipophilic additives, preservatives, antioxidants, solvents, fragrances, fillers, screening agents, odor absorbers and coloring materials. The amounts of these different additives and adjuvants are those conventionally used in the cosmetics field and, for example, range from 0.01% to 10% of the total weight of the composition. These additives and adjuvants, depending on their nature, can be introduced into the fatty phase, into the aqueous phase and/or into the lipid spherules.

Exemplary oils or waxes according to the invention include mineral oils (liquid petrolatum), vegetable oils (liquid fraction of karite butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin wax. Fatty alcohols and fatty acids (stearic acid) can be added to these oils.

Exemplary emulsifiers which are suitable according to the invention include glyceryl stearate, polysorbate 60 and the PEG-6/PEG-32/glycol stearate mixture marketed under the trademark Tefose®63 by Gattefosse.

Exemplary solvents which are suitable include the lower alcohols, in particular ethanol, isopropanol and propylene glycol.

Exemplary hydrophilic gelling agents according to the invention include carboxyvinyl polymers (carbomer), acrylic copolymers such as acrylate/alkyl acrylate copolymers, polyacrylamides, polysaccharides such as hydroxypropylcellulose, natural gums and clays. And exemplary lipophilic gelling agents include modified clays such as bentones, metal salts of fatty acids such as aluminum stearates, and hydrophobic silica, ethylcellulose or polyethylene.

The subject compositions can contain other hydrophilic active principles, such as proteins or protein hydrolysates, amino acids, polyols, urea, allantoin, sugars and sugar derivatives, water-soluble vitamins, plant extracts and hydroxy acids.

Representative lipophilic active principles include retinol (vitamin A) and derivatives thereof, tocopherol (vitamin E) and derivatives thereof, essential fatty acids, ceramides, essential oils or salicylic acid and derivatives thereof.

According to this invention, it is envisaged, inter alia, to combine at least one β-adrenergic agonist with other active agents suited, in particular, for the prevention and/or the treatment of cutaneous afflictions/conditions.

Exemplary such active agents include:

(1) agents which modulate cutaneous pigmentation and/or proliferation and/or differentiation, such as retinoic acid and isomers thereof, retinol and esters thereof, vitamin D and derivatives thereof, oestrogens, such as estradiol, kojic acid or hydroquinone;

(2) antibacterials, such as clindamycin phosphate, erythromycin or antibiotics from the tetracycline class;

(3) agents for combating parasites, in particular metronidazole, crotamiton or pyrethroids;

(4) antifungals, in particular compounds belonging to the imidazole class, such as econazole, ketoconazole or miconazole or salts thereof, polyene compounds, such as amphotericin B, compounds of the allylamine family, such as terbinafine, or octopirox;

(5) antiviral agents, such as acyclovir;

(6) steroidal anti-inflammatory agents, such as hydrocortisone, betamethasone valerate or clobetasol propionate, or non-steroidal anti-inflammatory agents, such as ibuprofen and salts thereof, diclofenac and salts thereof, acetylsalicylic acid, acetaminophen or glycyrrhetinic acid;

(7) anaesthetic agents, such as lidocaine hydrochloride and derivatives thereof;

(8) antipruriginous agents, such as thenaldine, trimeprazine or cyproheptadine;

(9) keratolytic agents, such as α- and β-hydroxycarboxylic acids or β-ketocarboxylic acids, their salts, amides or esters and, more particularly, hydroxy acids, such as glycolic acid, lactic acid, salicylic acid, citric acid and, generally, the fruit acids, and 5-(n-octanoyl)salicylic acid;

(10) agents for combating free radicals, such as α-tocopherol or esters thereof, superoxide dismutases, certain metal chelating agents or ascorbic acid and esters thereof;

(11) antiseborrhoeics, such as progesterone;

(12) antidandruff agents, such as octopirox or zinc pyrithione;

(13) antiacne agents, such as retinoic acid or benzoyl peroxide.

Thus, in a specific embodiment of the invention, the subject compositions comprise at least one β-adrenergic agonist and at least one active agent selected from among antibacterial agents, agents for combating parasites, antifungal agents, antiviral agents, anti-inflammatory agents, antipruriginous agents, anaesthetic agents, keratolytic agents, agents for combating free radicals, antiseborrhoeic agents, antidandruff agents, antiacne agents and/or agents which modulate cutaneous pigmentation and/or proliferation and/or differentiation.

Advantageously, at least one β-adrenergic agonist is combined with products or species eliciting an irritant effect and commonly used in the cosmetics or pharmaceutical industries, agents which are sometimes cosmetic or pharmaceutical active principles. The presence of a substance P antagonist in the form of at least one β-adrenergic agonist in a cosmetic or pharmaceutical composition comprising an active agent eliciting an irritant effect makes it possible to greatly reduce or indeed eliminate this irritant effect.

This additionally permits increasing the amount of active principle eliciting an irritant effect with respect to the amount of active principle normally used, for the purpose of improved effectiveness.

Thus, this invention also features cosmetic or pharmaceutical compositions, preferably for topical application, comprising, in a cosmetically or pharmaceutically acceptable medium (vehicle, diluent or carrier), at least one active agent eliciting an irritant effect, and further comprising at least one β-adrenergic agonist.

Exemplary active agents eliciting an irritant effect include surfactants (ionic or non-ionic), preservatives, organic solvents or active principles, such as α-hydroxy acids (citric, malic, glycolic, tartaric, mandelic or lactic acid), β-hydroxy acids (salicylic acid and derivatives thereof, α-keto acids, β-keto acids, retinoids (retinol, retinal or retinoic acid), anthralins (dioxyanthranol), anthranoids, peroxides (in particular benzoyl peroxide), minoxidil, lithium salts, antimetabolites, vitamin D and derivatives thereof, hair dyes or colorants (para-phenylenediamine and derivatives thereof or aminophenols), perfuming alcoholic solutions (fragrances, toilet waters, aftershaves or deodorants), antiperspirant agents (certain aluminum salts), depilatory or permanent-wave active principles (thiols) or depigmenting active principles (hydroquinone).

The incorporation of a substance P antagonist makes it possible in particular to multiply by a factor of 2 to 10 the amount of active principle eliciting an irritant effect with respect to the state of the art, without experiencing any of the discomforts mentioned above. Thus, it is possible to incorporate hydroxy acids up to 50% of the weight of the composition or retinoids up to 5%, while significantly reducing their irritant effect.

In these compositions, the β-adrenergic agonist is preferably formulated in an amount ranging from $10^{-8}\%$ to 10% by weight with respect to the total weight of the composition and, in particular, in an amount ranging from $10^{-5}\%$ to 4% by weight with respect to the total weight of the composition.

The compositions according to the invention comprising, in a cosmetically or pharmaceutically acceptable medium, at least one species eliciting an irritant effect and at least one β-adrenergic agonist can very obviously be formulated in any known pharmaceutical dosage form, such as, in particular, those described above.

The present invention also features a cosmetic treatment regimen for decreasing the irritant effect of a normally irritant compound, according to which a composition comprising at least one β-adrenergic agonist is topically applied onto the skin, onto the hair and/or onto the mucous membranes.

The present invention also features a cosmetic treatment regimen for decreasing the pain associated with an excess in the synthesis and/or in the release of substance P, also according to which a composition comprising at least one β-adrenergic agonist is topically applied onto the skin, onto the hair and/or onto the mucous membranes.

These cosmetic treatments are advantageously carried out by applying the cosmetic compositions described above according to the usual techniques. For example: application of sunscreen compositions or of makeup removal milks, lotions, serums, gels or creams onto the skin or onto dry hair, application of a hair lotion on wet hair or of shampoos, or, alternatively, application of a dentifrice onto the gums.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Pharmacological activity of a β-adrenergic agonist
In Vivo Functional Test with Respect to a Neurogenic Inflammation Model:

An in vivo functional test was carried out with respect to a neurogenic inflammation model in order to demonstrate the substance P antagonist nature of one of the β-adrenergic agonists, according to the technique described by X. J. Xu and coworkers (*Neurosciences*, 42, 731–737 (1991)).

The test entailed creating a neurogenic inflammation by the antidromic stimulation of the saphenous nerve in the anaesthetized animal. This nerve innervates the cutaneous regions of the hind paws.

The stimulation causes the release from the nerve endings of substance P, which is partially responsible for the neurogenic inflammation.

The neurogenic inflammation was quantified by measuring the tissular permeability with Evans blue, a marker for the tissular extravasation of plasma albumin which occurs during inflammation.

This reference model was used in the in vivo search for substance P antagonists.

The results of this study are reported in Table I below:

These results represent the mean of the results of 8 experiments.

TABLE I

| Compound | A | B | C | D | E | F |
|---|---|---|---|---|---|---|
| Concentration* | 5.98 ± 0.65 | 2.44 ± 0.56 | n.d. | n.d. | 1.37 ± 0.32 | 0.32 ± 0.62 |
| % of inhibition | 0% | 59% | 100% | 100% | 77% | 95% |
| Statistics |  | p < 0.01 | p < 0.001 | p < 0.001 | p < 0.001 | p < 0.001 |

A = Control (in the absence of any inhibitor)
B = Spantide II: 30 nmol (Reference SP antagonists)
C = Salbutamol: 1 μmol
D = Isoproterenol: 1 μmol
E = CGP12177.HCl: 1 μmol
F = Nylidrin.HCl: 1 μmol
*: expressed as μ/ml of Evans blue
n.d.: not detected These results evidence that, whatever the chemical structure of the various compounds of the β-adrenergic agonist family, all these molecules exert, always to a relatively large extent, an activity of substance P antagonist type.

EXAMPLE 2

Dose Effect of Salbutamol in the Antidromic Stimulation Model Presented in Example 1:

TABLE II

| Compound | Salbutamol | | | | Spantide II |
|---|---|---|---|---|---|
| Dose | 0.1 nmol | 1 nmol | 10 nmol | 100 nmol | 30 nmol |
| % of inhibition | 17% | 65% | 80% | 100% | 67% |
| Statistics | n.s. | p < 0.05 | p < 0.01 | p < 0.01 | p < 0.01 | n.s.: not significant.

The results evidence that the activity of salbutamol with respect to the release of substance P is dose dependent.

They also demonstrate a very high activity, approximately 30 times greater than that of the reference molecule, Spantide II.

EXAMPLE 3

Examples of specific formulations according to the invention. These compositions were prepared simply by intimately admixing the various components.

Composition 1: Antipruriginous Lotion:

| (a) Salbutamol | 0.10% |
|---|---|
| (b) Antioxidant | 0.05% |
| (c) Isopropanol | 40.00% |
| (d) Preservative | 0.30% |
| (e) Water | q.s. for 100% |

Composition 2: Gel for the Treatment of Psoriasis:

| (a) Salbutamol | 0.10% |
|---|---|
| (b) Hydroxypropylcellulose (Klucel H, marketed by Hercules) | 1.00% |
| (c) Antioxidant | 0.05% |
| (d) Isopropanol | 40.00% |
| (e) Preservative | 0.30% |
| (f) Water | q.s. for 100% |

Composition 3: Cream for Caring for the Face (oil-in-water emulsion):

| (a) Isoproterenol | 0.50% |
|---|---|
| (b) Glyceryl stearate | 2.00% |
| (c) Polysorbate 60 (Tween 60, marketed by ICI) | 1.00% |
| (d) Stearic acid | 1.40% |
| (e) Triethanolamine | 0.70% |
| (f) Carbomer | 0.40% |
| (g) Liquid fraction from karite butter | 12.00% |
| (h) Perhydrosqualene | 12.00% |
| (i) Antioxidant | 0.05% |
| (j) Fragrance | 0.50% |
| (k) Preservative | 0.30% |
| (l) Water | q.s. for 100% |

Composition 4: Shampoo:

| (a) Salbutamol | 0.05% |
|---|---|
| (b) Na lauryl ether sulfate (2.2 EO) | 12.00% |
| (c) Hydroxypropylcellulose (Klucel H, marketed by Hercules) | 1.00% |
| (d) Fragrance | 0.50% |
| (e) Preservative | 0.30% |
| (f) Water | q.s. for 100% |

Composition 5: Pain-control Gel:

| (a) Salbutamol | 0.25% |
|---|---|
| (b) Hydroxypropylcellulose (Klucel H, marketed by Hercules) | 1.00% |
| (c) Antioxidant | 0.05% |
| (d) Lidocaine hydrochloride | 2.00% |
| (e) Isopropanol | 40.00% |
| (f) Preservative | 0.30% |
| (g) Water | q.s. for 100% |

Composition 6: Cream for Treating Sunburn (oil-in-water emulsion):

| (a) Isoproterenol | 0.001% |
|---|---|
| (b) Glyceryl stearate | 2.00% |
| (c) Polysorbate 60 (Tween 60, marketed by ICI) | 1.00% |
| (d) Stearic acid | 1.40% |
| (e) Glycyrrhetinic acid | 2.00% |
| (f) Triethanolamine | 0.70% |
| (g) Carbomer | 0.40% |
| (h) Liquid fraction from karite butter | 12.00% |
| (i) Sunflower oil | 10.00% |
| (j) Antioxidant | 0.05% |
| (k) Fragrance | 0.50% |
| (l) Preservative | 0.30% |
| (m) Water | q.s. for 100% |

Composition 7: O/W Emulsion for the Treatment of the Skin of the Face:

Fatty phase:

| (a) Apricot kernel oil (triglycerides of oleic/linoleic acids) | 14.50% |
|---|---|
| (b) Liquid fraction from karite butter (triglycerides of palmitic/stearic/oleic/linoleic acids) | 7.00% |
| (c) Propyl para-hydroxybenzoate (preservative) | 0.10% |
| (d) Fatty alcohol mixture (stearyl alcohol, arachidyl alcohol, behenyl alcohol) | 1.00% |
| (e) Sorbitan monostearate (Span 60 marketed by ICI) | 2.50% |
| (f) Mixture of cetylstearyl 2-ethylhexanoate and isopropyl myristate (purcellin oil) | 2.00% |

Aaueous phase:

| (g) Preservatives | 0.50% |
|---|---|
| (h) Disodium salt of ethylenediaminetetraacetic acid $2H_2O$ (complexing agents) | 0.05% |
| (i) Neutralizing agent | 0.50% |
| (j) Gelling agent | 0.70% |
| (k) Glycerol | 5.00% |
| (l) Oxyethylenated (20 EO) sorbitan monostearate (Tween 60 marketed by ICI) (surfactant) | 2.50% |
| (m) 5-(n-Octanoyl)salicylic acid | 1.00% |
| (n) Salbutamol | 0.05% |
| (o) Demineralized or deionized water | q.s. for 100% |

Composition 8: O/W Emulsion for the Treatment of the Skin of the Face:

Fatty phase:

| (a) Apricot kernel oil (triglycerides of oleic/linoleic acids) | 14.50% |
|---|---|
| (b) Liquid fraction from karite butter (triglycerides of palmitic/stearic/oleic/linoleic acids) | 7.00% |
| (c) Propyl para-hydroxybenzoate (preservative) | 0.10% |
| (d) Fatty alcohol mixture (stearyl alcohol, arachidyl alcohol, behenyl alcohol) | 1.00% |
| (e) Sorbitan monostearate (Span 60 marketed by ICI) | 2.50% |
| (f) Mixture of cetylstearyl 2-ethylhexanoate and isopropyl myristate (purcellin oil) | 2.00% |

Aqueous phase:

| (g) Preservatives | 0.50% |
|---|---|
| (h) Disodium salt of ethylenediaminetetraacetic acid $2H_2O$ (complexing agents) | 0.05% |
| (i) Neutralizing agent | 0.50% |
| (j) Gelling agent | 0.70% |
| (k) Glycerol | 5.00% |
| (l) Oxyethylenated (20 EO) sorbitan monostearate (Tween 60 marketed by ICI) (surfactant) | 2.50% |
| (m) Retinoic acid | 0.025% |
| (n) Salbutamol | 0.05% |
| (o) Demineralized or deionized water | q.s. for 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for the treatment of a mammalian cutaneous disorder, a manifestation of which is at least one of the following: excess in the synthesis of substance P, and an excess in the release of substance P, comprising administering at least one β-adrenergic antagonist selected from the group consisting of salbutamol, 4-[3-[(1,1-dimethylethyl)amino]-2-hydroxypropyl]-1,3-dihydro-2H-benzimidazol-2-one hydrochloride], nylidrin, salmeterol, fenoterol, terbutaline, pirbuterol, and combinations thereof, wherein said disorder is selected from the group consisting of pruriginous diseases, urticaria, atopic dermatitides, contact dermatitides, pruriginous dermatoses, and erythemal dermatoses, comprising administering a therapeutically effective amount of at least one β-adrenergic antagonist.

2. The method as defined by claim 1, comprising topically applying said at least one β-adrenergic agonist onto the skin, the hair and/or the mucous membranes of said mammalian organism.

3. The method as defined by claim 1, wherin said at least one β-adrenergic agonist is salbutamol.

4. The method as defined by claim 1, comprising coadministering to said mammalian organism at least one antibacterial active agent, at least one active agent for combating parasites, at least one antifungal active agent, at least one antiviral active agent, at least one anti-inflammatory active agent, at least one antipruriginous active agent, at least one anaesthetic active agent, at least one keratolytic active agent, at least one active agent for combating free radicals, at least one antiseborrhoeic active agent, at least one antidandruff active agent, at least one antiacne active agent and at least one active agent which modulates at lesast on of cutaneous pigmentation or proliferation or differentiation.

* * * * *